(12) United States Patent
Lund et al.

(10) Patent No.: US 10,813,762 B2
(45) Date of Patent: Oct. 27, 2020

(54) INFLATABLE PENILE PROSTHESIS WITH REINFORCED CYLINDER

(71) Applicant: Boston Scientific Scimed, Inc., Maple Grove, MN (US)

(72) Inventors: Jonathan J. Lund, Glencoe, MN (US); Matthew Lee Nelson, Plymouth, MN (US); Douglas Lawrence Evans, Andover, MN (US); Mark Edward DiLoreto, Chaska, MN (US); Thomas Andrew Albrecht, Edina, MN (US); Paul J. Gindele, Buffalo, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 113 days.

(21) Appl. No.: 16/139,747

(22) Filed: Sep. 24, 2018

(65) Prior Publication Data

US 2019/0091025 A1 Mar. 28, 2019

Related U.S. Application Data

(60) Provisional application No. 62/563,384, filed on Sep. 26, 2017.

(51) Int. Cl.
*A61F 2/26* (2006.01)

(52) U.S. Cl.
CPC ........ *A61F 2/26* (2013.01); *A61F 2250/0003* (2013.01)

(58) Field of Classification Search
CPC ......... A61F 2/26; A61F 5/41; A61F 2005/415
USPC ....................................... 600/38–41
See application file for complete search history.

(56) References Cited

U.S. PATENT DOCUMENTS

| 4,267,829 A | 5/1981 | Burton et al. |
| 5,112,295 A | 5/1992 | Zinner et al. |
| 2005/0014993 A1 | 1/2005 | Mische et al. |

OTHER PUBLICATIONS

International Search Report and Written Opinion for International Application No. PCT/US2018/052673, dated Jan. 2, 2019, 17 pages.

*Primary Examiner* — John P Lacyk
(74) *Attorney, Agent, or Firm* — Brake Hughes Bellermann LLP

(57) ABSTRACT

According to an aspect, an implant including an inflatable member and a pump assembly configured to facilitate a transfer of a fluid from the reservoir to the inflatable member. The inflatable member defines a lumen and includes a structural member. At least a portion of the structural member is disposed within the lumen defined by the inflatable member. In some implementations, the implant includes a reservoir configured to hold fluid.

19 Claims, 10 Drawing Sheets

INFLATABLE PENILE PROSTHESIS WITH REINFORCED CYLINDER

CROSS-REFERENCE TO RELATED APPLICATION

This application is a Nonprovisional of, and claims priority to, U.S. Patent Application No. 62/563,384, filed on Sep. 26, 2017, entitled "INFLATABLE PENILE PROSTHESIS WITH REINFORCED CYLINDER", which is incorporated by reference herein in its entirety

TECHNICAL FIELD

This disclosure relates generally to bodily implants and more specifically to bodily implants, such as penile prostheses that include inflatable members.

BACKGROUND

One treatment for male erectile dysfunction is the implantation of a penile prosthesis that mechanically erects the penis. Some existing penile prostheses include inflatable cylinders or members that can be inflated or deflated using a pump mechanism. In some existing devices, the inflatable cylinder or member requires a relatively large amount of force to inflate. Additionally, in some existing devices, the pump mechanism may require many sequential squeezes or activations to inflate the cylinder or member.

Accordingly, it would be useful to provide a bodily implant, such as a penile prosthesis that includes an improved cylinder or member that can be more easily inflated.

SUMMARY

According to an aspect, an implant including an inflatable member and a pump assembly configured to facilitate a transfer of a fluid from the reservoir to the inflatable member. The inflatable member defines a lumen and includes a structural member. At least a portion of the structural member is disposed within the lumen defined by the inflatable member. In some implementations, the implant includes a reservoir configured to hold fluid.

In some embodiments, the structural member is flexible. In some embodiments, the structural member is a suture.

In some embodiments, the inflatable member includes a sidewall that defines the lumen, the structural member includes a first portion coupled to a first portion of the sidewall, the structural member includes a second portion coupled to a second portion of the sidewall.

In some embodiments, the structural member is a first structural member, the inflatable member including a second structural member disposed within the lumen. In some embodiments, the structural member is a first structural member, the inflatable member including a second structural member disposed within the lumen, the first structural member being disposed substantially parallel to the second structural member. In some embodiments, the structural member is a first structural member, the inflatable member including a second structural member disposed within the lumen, the first structural member being disposed substantially perpendicular to the second structural member.

In some embodiments, the inflatable member extends along a longitudinal axis, the structural member is a first structural member, the inflatable member including a second structural member disposed within the lumen, the first structural member is longitudinally spaced from the second structural member. In some embodiments, the inflatable member includes a sidewall that is formed of a woven fabric, the inflatable member includes a coating disposed on an outer surface of the sidewall. In some embodiments, the inflatable member includes a sidewall that is formed of a woven fabric, the structural member extends through the sidewall at a first location and extends through the sidewall at a second location, the first location being different than the first location.

In some embodiments, the implant includes a first cap coupled to a first end portion of the inflatable member, and a second cap coupled to a second end portion of the inflatable member.

In some embodiments, the structural member is a first structural member, the inflatable member including a second structural member and a third structural member, the second structural member being disposed within the lumen, the third structural member being disposed within the lumen. In some embodiments, the structural member is a first structural member, the inflatable member including a second structural member and a third structural member, the second structural member being disposed within the lumen, the third structural member being disposed within the lumen, the first structural member being offset from the second structural member and the third structural member, the second structural member being offset from the third structural member.

In some embodiments, the pump is configured to help facilitate a transfer of the fluid from the inflatable member to the reservoir when the implant is in a deflation mode. In some embodiments, the pump assembly includes a valve housing and a pump bulb member.

According to another aspect, a bodily implant includes an inflatable member, the inflatable member defining a lumen and including a structural member, at least a portion of the structural member being disposed within the lumen defined by the inflatable member.

In some embodiments, the inflatable member includes a sidewall that is formed of a woven fabric, the structural member extends through the sidewall at a first location and extends through the sidewall at a second location, the first location being different than the first location. In some embodiments, the inflatable member includes a sidewall that is formed of a woven fabric, the structural member extends through the sidewall at a first location and extends through the sidewall at a second location, the first location being different than the first location, a coating being disposed on an outer surface of the fabric.

According to another aspect, a method of making a bodily implant includes providing a member that includes a sidewall that defines a lumen; and passing a structural member through the member at a first location of the member. In some embodiments, the method includes passing the structural member through the member at a second location of the member, the second location of the member being different than the first location of the member.

DETAILED DESCRIPTION

Figure 1A:
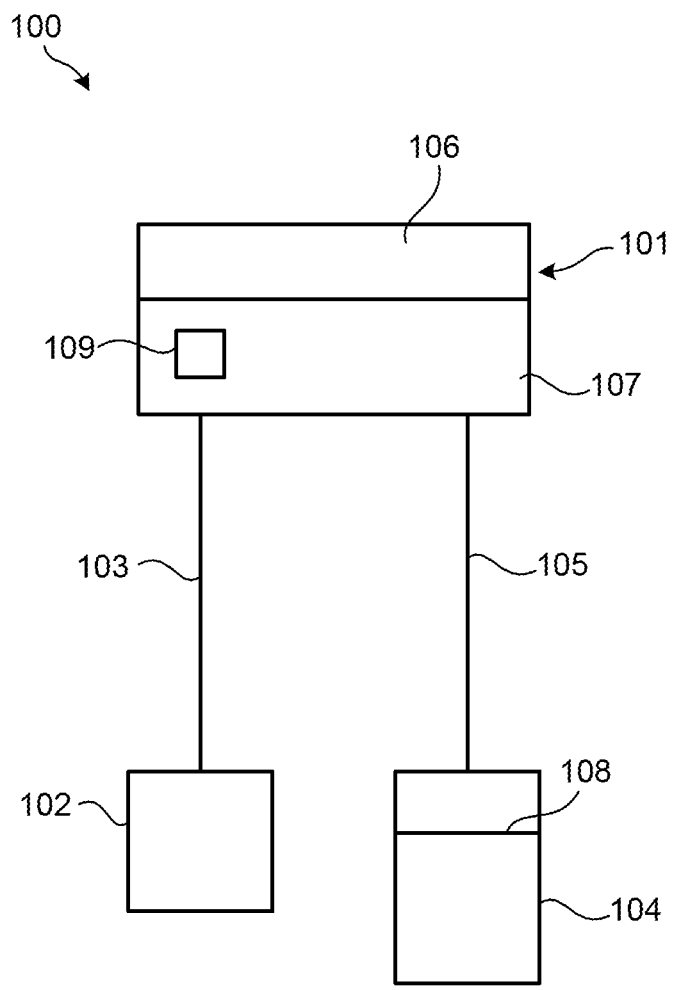
FIG. 1A schematically illustrates an penile prosthesis according to an embodiment.

Detailed embodiments are disclosed herein. However, it is understood that the disclosed embodiments are merely examples, which may be embodied in various forms. Therefore, specific structural and functional details disclosed herein are not to be interpreted as limiting, but merely as a basis for the claims and as a representative basis for teaching one skilled in the art to variously employ the embodiments in virtually any appropriately detailed structure. Further, the terms and phrases used herein are not intended to be limiting, but to provide an understandable description of the present disclosure.

The terms "a" or "an," as used herein, are defined as one or more than one. The term "another," as used herein, is defined as at least a second or more. The terms "including" and/or "having", as used herein, are defined as comprising (i.e., open transition). The term "coupled" or "moveably coupled," as used herein, is defined as connected, although not necessarily directly and mechanically.

In general, the embodiments are directed to medical devices such as penile prostheses or other bodily implants. The term patient or user may hereafter be used for a person who benefits from the medical device or the methods disclosed in the present disclosure. For example, the patient can be a person whose body is implanted with the medical device or the method disclosed for operating the medical device by the present disclosure. For example, in some embodiments, the patient may be a human male, a human female, or any other mammal.

The terms proximal and distal described in relation to various devices, apparatuses, and components as discussed in the subsequent text of the present disclosure are referred with a point of reference. The point of reference, as used in this description, is a perspective of a person who implants the inflatable penile prosthesis. The person may be a surgeon, a physician, a nurse, a doctor, a technician, and the like who may perform the implantation procedure. The term proximal refers to an area or portion that is closer or closest to the person during the implantation procedure. The term distal refers to an area or portion that is farther or farthest from the person.

The embodiments discussed herein may improve the performance of an inflatable member of the device. For example, the inflatable member may have improved stiffness or rigidity, improved reliability, or improved deflation or inflation times. In some embodiments, the inflatable member may be facilitated by requiring less force or pressure to inflate the inflatable member.

The embodiments may include an inflatable penile prosthesis having a pump assembly, an inflatable member, and a reservoir. The inflatable member may be implanted into the corpus cavernosae of a patient or user, the reservoir may be implanted in the user's abdomen, and the pump assembly may be implanted in the scrotum. The pump assembly may switch between an inflation position and a deflation position such that a user can operate the device to place the inflatable penile prosthesis in either an inflation mode to transfer fluid from the reservoir to the inflatable member or a deflation mode to transfer the fluid from the inflatable member back to the reservoir.

FIG. 1A schematically illustrates an inflatable penile prosthesis 100 according to an aspect. The inflatable penile prosthesis 100 may include a reservoir 102, a cylinder or inflatable member 104, and a pump assembly 101 configured to transfer fluid between the reservoir 102 and the inflatable member 104. In some examples, the inflatable member 104 may be implanted into the corpus cavernosae of the user, the reservoir 102 may be implanted in the abdomen or pelvic cavity of the user (e.g., the reservoir 102 may be implanted in the lower portion of the user's abdominal cavity or the upper portion of the user's pelvic cavity), and the pump assembly 101 may be implanted in the scrotum of the user.

The inflatable member 104 may be capable of expanding upon the injection of fluid into a cavity of the inflatable member 104. For instance, upon injection of the fluid into the inflatable member 104, the inflatable member 104 may increase its length and/or width, as well as increase its rigidity. In some examples, the inflatable member 104 may include a pair of cylinders or at least two cylinders, e.g., a first cylinder member and a second cylinder member. The volumetric capacity of the inflatable member 104 may depend on the size of the cylinders. In some examples, the volume of fluid in each cylinder may vary from about 10 milliliters in smaller cylinders and to about 50 milliliters in larger sizes. In some examples, the first cylinder member may be larger than the second cylinder member. In other examples, the first cylinder member may have the same size as the second cylinder member.

In some embodiments, the inflatable member 104 includes a structural member 108. In some embodiments, the structural member 108 provides support to the inflatable member 104. For example, the structural member 108 may provide support to the inflatable member 104 when the inflatable member is placed in its inflated configuration. In some embodiments, the structural member 108 may facilitate the inflation of the inflatable member 104. For example, the structural member 108 may allow the inflatable member to be inflated at a relatively low pressure. In some embodiments, this may allow the user to inflate the inflatable member 104 with less pumps or activations of the pump or may allow the user to apply less force to the pump to inflate the inflatable member 104. Details of the pump assembly 101 are described below.

In some embodiments, the structural member 108 is at least partially disposed within the cavity or lumen of the inflatable member 104. For example, in some embodiments, the structural member 108 may extend from one portion of the inflatable member 104 to another portion of the inflatable member 104.

In some embodiments, the inflatable member 104 includes more than one structural member 108. For example, the inflatable member 104 may include two, three, four, or many structural members. In some embodiments, the structural members 108 are disposed apart from each other and extend along a length or longitudinal axis of the inflatable member 104. In some embodiments, one of the structural members is disposed offset or at an angle with respect to another of the structural members. In other embodiments, one of the structural members is disposed parallel to or substantially parallel to another of the structural members.

In some embodiments, the structural member 108 is flexible. In some embodiments, the structural member 108 is formed of a suture or other filament. In other embodiments, the structural member 108 is formed of another material. In some embodiments, the structural member 108 is formed of an elastic material. In other embodiments, the structural member 108 is formed of a non-elastic material.

The reservoir 102 may include a container having an internal chamber configured to hold or house fluid that is used to inflate the inflatable member 104. The volumetric capacity of the reservoir 102 may vary depending on the size of the inflatable penile prosthesis 100. In some examples, the volumetric capacity of the reservoir 102 may be 3 to 150 cubic centimeters. In some examples, the reservoir 102 is constructed from the same material as the inflatable member 104. In other examples, the reservoir 102 is constructed from a different material than the inflatable member 104.

The inflatable penile prosthesis 100 may include a first conduit connector 103 and a second conduit connector 105. Each of the first conduit connector 103 and the second conduit connector 105 may define a lumen configured to transfer the fluid to and from the pump assembly 101. The first conduit connector 103 may be coupled to the pump assembly 101 and the reservoir 102 such that fluid can be transferred between the pump assembly 101 and the reservoir 102 via the first conduit connector 103. For example, the first conduit connector 103 may define a first lumen configured to transfer fluid between the pump assembly 101 and the reservoir 102. The first conduit connector 103 may include a single or multiple tube members for transferring the fluid between the pump assembly 101 and the reservoir 102.

The second conduit connector 105 may be coupled to the pump assembly 101 and the inflatable member 104 such that fluid can be transferred between the pump assembly 101 and the inflatable member 104 via the second conduit connector 105. For example, the second conduit connector 105 may define a second lumen configured to transfer fluid between the pump assembly 101 and the inflatable member 104. The second conduit connector 105 may include a single or multiple tube members for transferring the fluid between the pump assembly 101 and the inflatable member 104. In some examples, the first conduit connector 103 and the second conduit connector 105 may include a silicone rubber material.

The pump assembly 101 may switch between an inflation mode in which the fluid in the reservoir 102 is transferred to the inflatable member 104 through the pump assembly 101 in a first direction (e.g., inflation direction) and a deflation mode in which the fluid in the inflatable member 104 is transferred back to the reservoir 102 through the pump assembly 101 in a second direction (e.g., deflation direction).

The pump assembly 101 includes a pump (also referred to as a pump bulb member) 106 and a valve body 107. The valve body 107 also includes a selection member 109. The selection member 109 may be used to select or change the mode in which the pump assembly is in. For example, the selection member 109 may be moved from a first position to a second position to place the device in its deflation mode. The selection member 109 may then be moved back to its first position to place the device in its inflation mode. In some embodiments, the selection member 109 is movable with respect to the valve body 107. For example, in some embodiments, the selection member 109 is slidably coupled or slideable with respect to the valve body 107.

The pump 106 may be squeezed or depressed by the user in order to facilitate the transfer of fluid from the reservoir 102 to the inflatable member 104. For example, in the inflation mode, while the user is operating the pump 106, the pump 106 may receive the fluid from the reservoir 102, and then output the fluid to the inflatable member 104. When the user switches to the deflation mode, at least some of the fluid can automatically be transferred back to the reservoir 102 (due to the difference in pressure from the inflatable member 104 to the reservoir 102). Then, the user may squeeze the inflatable member 104 to facilitate the further transfer of fluid through the pump 106 to the reservoir 102.

In some examples, the pump 106 may include a flexible member defining a cavity. In some examples, the pump 106 may define a pump shell having a flexible bulb and a valve body connector, where the valve body connector is designed to fit at least partially over the valve body 107. In some examples, the pump 106 may include a squeeze pump. In some examples, the pump 106 may include a portion that is round or substantially round. In some examples, the pump 106 may include ribbing or dimples to aid the user in gripping the pump 106. The pump 106 may use suction and pressure to move the fluid in and out of the cavity of the pump 106 in the inflation mode. For example, the user may depress or squeeze the pump 106 to expel the fluid out of the cavity, and, when the flexible member returns to its original shape, the resulting suction pushes the fluid into the cavity of the pump 106. In some examples, the pump 106 may have a bulb spring rate that is designed to refill the pump 106 in a selected time frame.

As discussed above, the selection member 109 may be used to select or change the mode in which the pump assembly is in. For example, in one embodiment, the selection member 109 may be placed in the inflate position and the user may then operate the pump 106 to inflate the inflatable member 104 (i.e., move the fluid from the reservoir 102 to the inflatable member 104). For example, the user may repeatedly depress or squeeze the pump 106 until the desired rigidity is achieved.

In some examples, if the reservoir 102 is at least partially pressurized, the fluid may automatically flow out of the reservoir 102 and into the inflatable member 104 without the user depressing or squeezing the pump 106 until the pressure is at least partially equalized between the reservoir 102 and the inflatable member 104.

Then, when the user wants to deflate the inflatable member 104, the user moves selection member 109 to its deflated position. The user may then operate the pump 106 to deflate the inflatable member 104 (i.e., move the fluid from the inflatable member 104 to the reservoir 102). The pump 106 may then return to its original form, which provides a suction force causing fluid to be drawn into the pump 106 from the inflation member 104. The fluid from the inflation member 104 fills the pump 106 (or at least partially fills the pump 106). This pump cycle is repeated until the inflatable member 104 is deflated.

In some examples, the fluid may automatically (upon movement of the selection member 109 to its deflate position) flow out of the inflatable member 104 and into the reservoir 102 without the user depressing or squeezing the pump 106 until the pressure is at least partially equalized between the reservoir 102 and the inflatable member 104.

In some examples, after the inflation member 104 has been deflated, the pump 106 may be squeezed to place the pump in a contracted position or configuration.

Figure 1B:
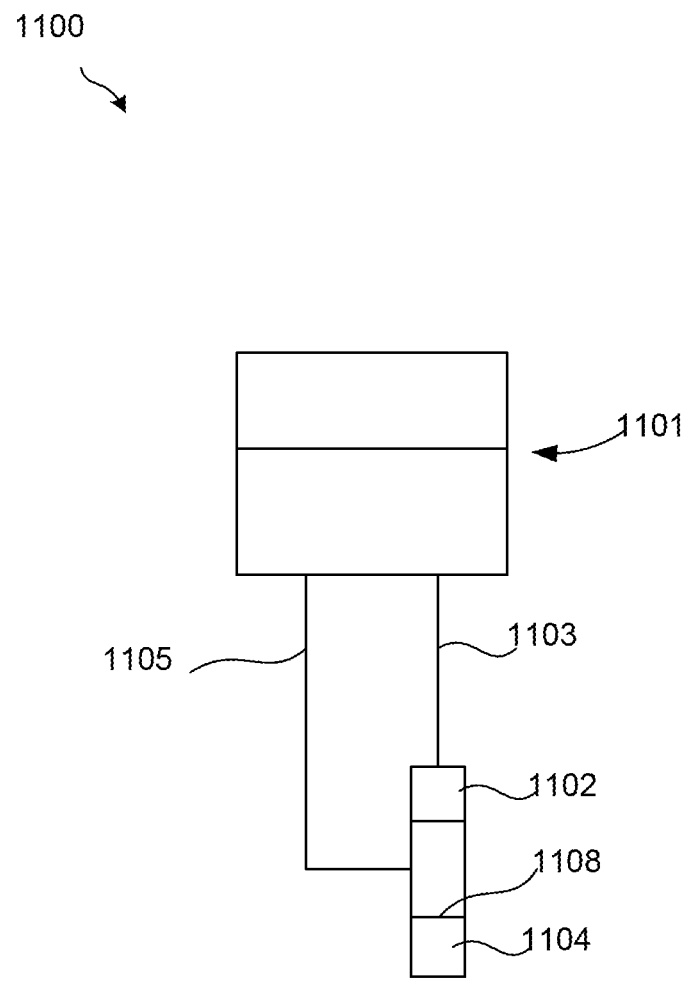
FIG. 1B schematically illustrates a penile prosthesis according to another embodiment.

FIG. 1B schematically illustrates an inflatable penile prosthesis 1100 according to another aspect. The inflatable penile prosthesis 1100 includes a reservoir 1102, a cylinder or inflatable member 1104, and a pump assembly 1101 configured to transfer fluid between the reservoir 1102 and the inflatable member 1104. In some examples, the inflatable member 1104 and the reservoir 1102 may be located adjacent to each other or may be portions of the same unit or member. In this embodiment, the inflatable member 1104 and the reservoir 1102 may be implanted into the corpus cavernosae of the user and the pump assembly 1101 may be implanted in the scrotum of the user. In the illustrated embodiment, the inflatable member 1104, the reservoir 1102, and the pump assembly 1101 may be fluidically coupled via fluid connectors 1103 and 1105. In the illustrated embodiments, the inflatable member 1104 includes a structural member 1108.

Figure 2:
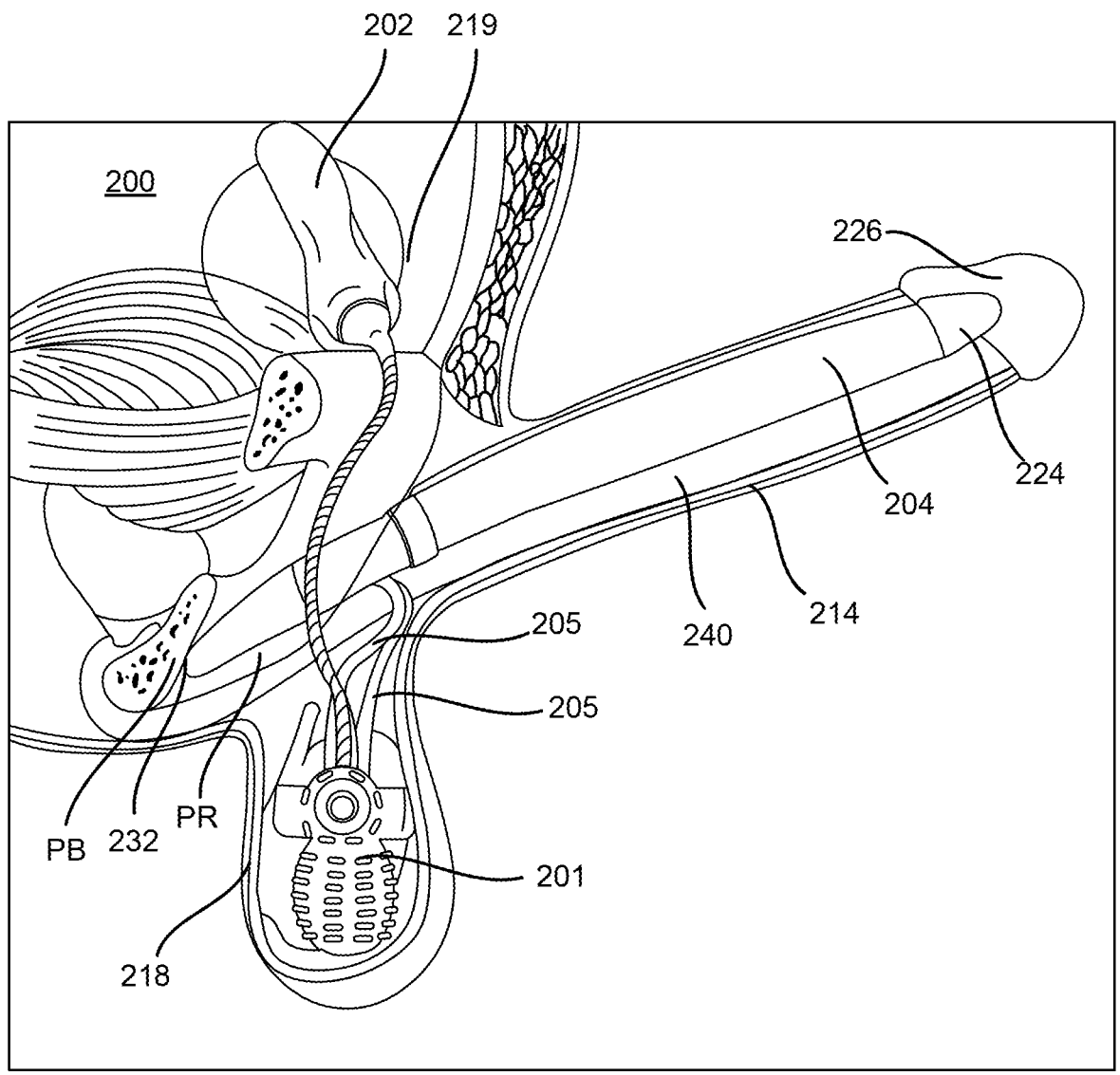
FIG. 2 illustrates a penile prosthesis implanted within a patient according to an embodiment.
Figure 3:
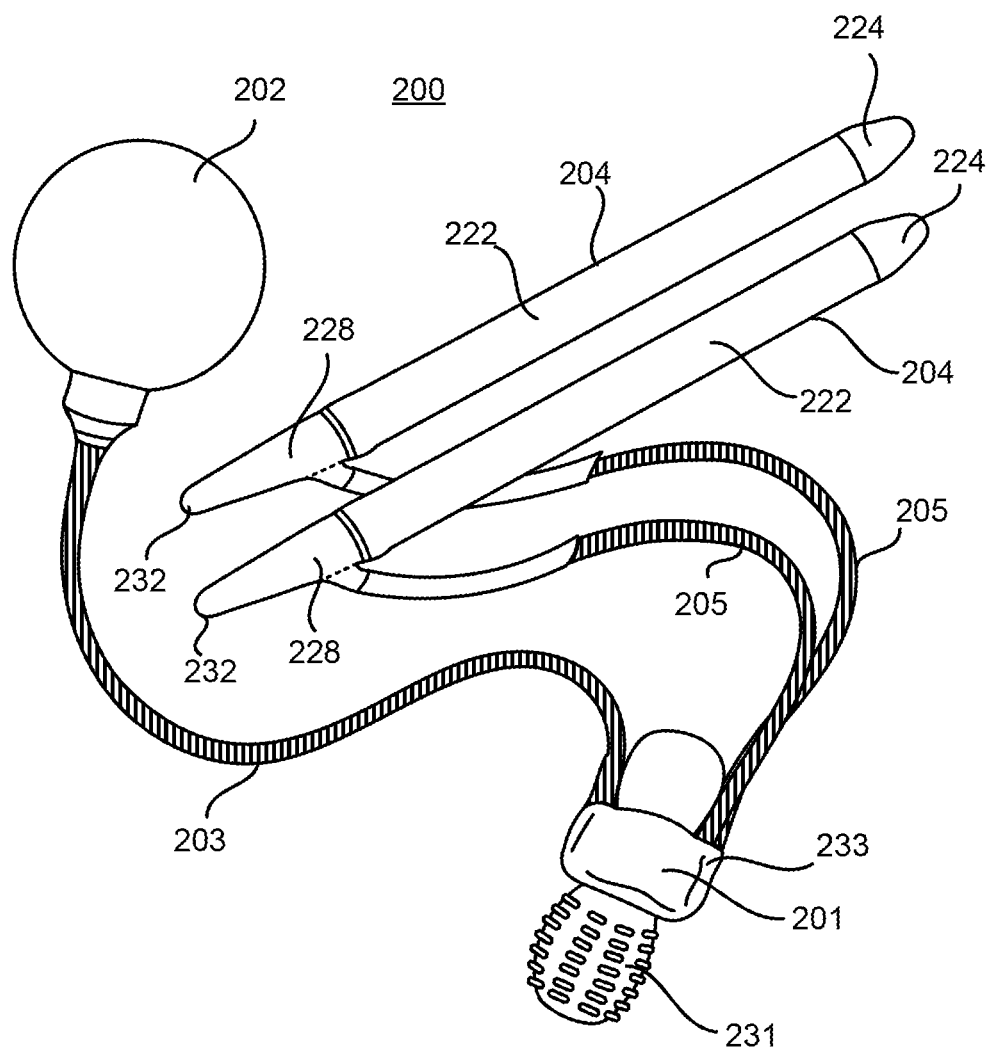
FIG. 3 is a perspective view of the penile prosthesis of FIG. 2.

FIG. 2 illustrates a penile prosthesis 200 implanted within a user according to an aspect. FIG. 3 is a perspective view of the penile prosthesis 200. FIGS. 4, 5, 6A, and 7 illustrate portions of an inflatable member of the penile prosthesis.

The penile prosthesis 200 may include a pair of cylinders 204, and the pair of cylinders or inflatable members 204 are implanted in a penis 214. For example, one of the cylinders 204 may be disposed on one side of the penis 214. The other cylinder 204 (not shown in FIG. 2) of the pair of cylinders may be disposed on the other side of the penis 214. The cylinder 204 may include a distal end portion 224, a cavity or inflation chamber 222, and a proximal end portion 228 having a rear tip 232.

The penile prosthesis 200 may include a pump assembly 201, which may be implanted into the patient's scrotum 218. A pair of conduit connectors 205 may attach the pump assembly 201 to the pair of inflatable members or cylinders 204 such that the pump assembly 201 is in fluid communication with the pair of inflatable members or cylinders 204. Also, the pump assembly 201 may be in fluid communication with a reservoir 202 via a conduit connector 203. The reservoir 202 may be implanted into the user's abdomen 219. The inflation chamber or portion 222 of the cylinder 204 may be disposed within the penis 214. The distal end portion 224 of the cylinder 204 may be at least partially disposed within the crown portion 226 of the penis 214. The proximal end portion 228 may be implanted into the patient's pubic region PR with the rear tip 232 proximate the pubic bone PB.

In order to implant the inflatable members or cylinders 204, the surgeon first prepares the patient. The surgeon often makes an incision in the penoscrotal region, e.g., where the base of the penis 214 meets with the top of the scrotum 218. From the penoscrotal incision, the surgeon may dilate the patient's corpus cavernosae 240 to prepare the patient to receive the pair of inflatable members or cylinders 204. The corpus cavernosum is one of two parallel columns of erectile tissue forming the dorsal part of the body of the penis 214, e.g., two slender columns that extend substantially the length of the penis 214. The surgeon will also dilate two regions of the pubic area (proximal corpora cavernosae) to prepare the patient to receive the proximal end portion 228. The surgeon may measure the length of the proximal and distal corpora cavernosae from the incision and the dilated region of the pubic area to determine an appropriate size of the inflatable members or cylinders 204 to implant.

After the patient is prepared, the penile prosthesis 200 is implanted into the patient. The distal tip of the distal end portion 224 of each cylinder 204 may be attached to a suture. The other end of the suture may be attached to a needle member (e.g., Keith needle). The needle member is inserted into the incision and into the dilated corpus cavernosum. The needle member is then forced through the crown of the penis 214. The surgeon tugs on the suture to pull the cylinder 204 into the corpus cavernosum. This is done for each cylinder of the pair of cylinders 204. Once the inflation chamber 222 is in place, the surgeon may remove the suture from the distal tip. The surgeon then inserts the proximal end portion 228. The surgeon inserts the rear end of the cylinder 204 into the incision and forces the proximal end portion 228 toward the pubic bone PB until each cylinder 204 is in place.

In the illustrated embodiment, each of the inflatable members or cylinders 204 is structurally and functionally similar. Accordingly, only one of the inflatable members or cylinders will be discussed in detail. The inflatable member 204 may be capable of expanding upon the injection of fluid into a cavity of the inflatable member 204. For instance, upon injection of the fluid into the inflatable member 204, the inflatable member 204 may increase its length and/or width, as well as increase its rigidity. The volumetric capacity of the inflatable member 204 may depend on the size of the cylinders. In some examples, the volume of fluid in each cylinder may vary from about 10 milliliters in smaller cylinders and to about 50 milliliters in larger sizes.

In the illustrated embodiment, the inflatable member 204 includes a sidewall 280 that defines a lumen or cavity 282. The inflatable member 204 also includes a plurality of structural members 284. In some embodiments, the structural members 284 provide support to the inflatable member 204. For example, the structural members 284 may provide support to the inflatable member 204 when the inflatable member is placed in its inflated configuration. In some embodiments, the structural members 284 may facilitate the inflation of the inflatable member 204. For example, the structural members 284 may allow the inflatable member 204 to be inflated at a relatively low pressure. In some embodiments, this may allow the user to inflate the inflatable member 204 with less pumps or activations of the pump or may allow the user to apply less force to the pump to inflate the inflatable member 204. Details of the pump assembly 201 are described below.

In the illustrated embodiment, the structural members 284 are at least partially disposed within the cavity or lumen 282 of the inflatable member 204. For example, in some embodiments, the structural member 284 may extend from one portion of the inflatable member 204 to another, different portion of the inflatable member 204. Specifically, for example, one structural member may extend from a first portion of the sidewall 280 to a second, different portion of the sidewall 280. In some embodiments, the structural member has a first portion that is coupled to the first portion of the sidewall 280 and a second portion that is coupled to the second portion of the sidewall 280. In some embodiments, the structural members may extend through a center of the lumen 282. In other embodiments, the structural members extend adjacent to the center of the lumen 282.

The inflatable member 204 may include any number of structural members 284. In some embodiments, the structural members 284 may be different, separate members or pieces of material. In other embodiments, the structural members 284 may be a single unitary member that is passed through or coupled to the sidewall at various locations.

Figure 4:
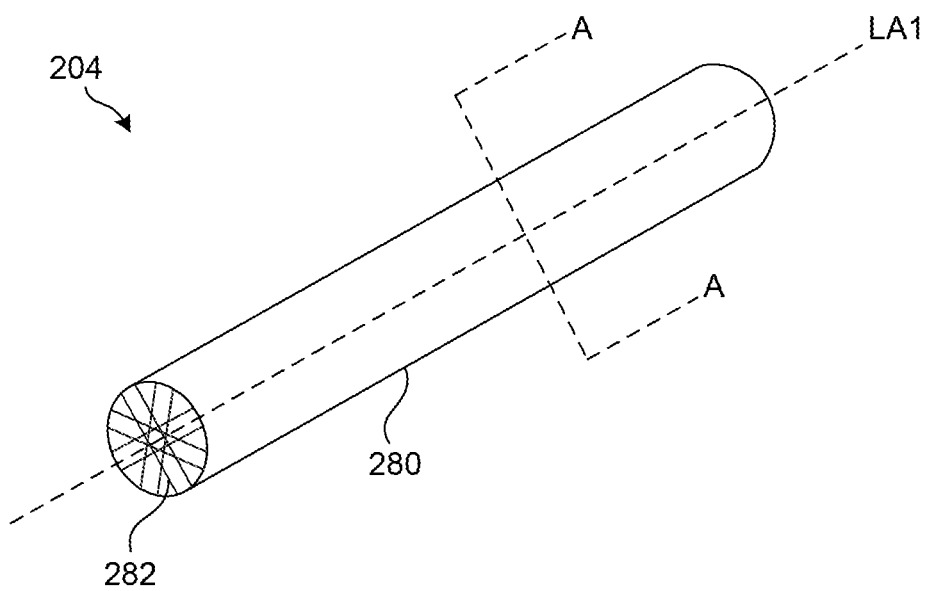
FIG. 4 is a perspective view of an inflatable member of the penile prosthesis of FIG. 2.
Figure 5:
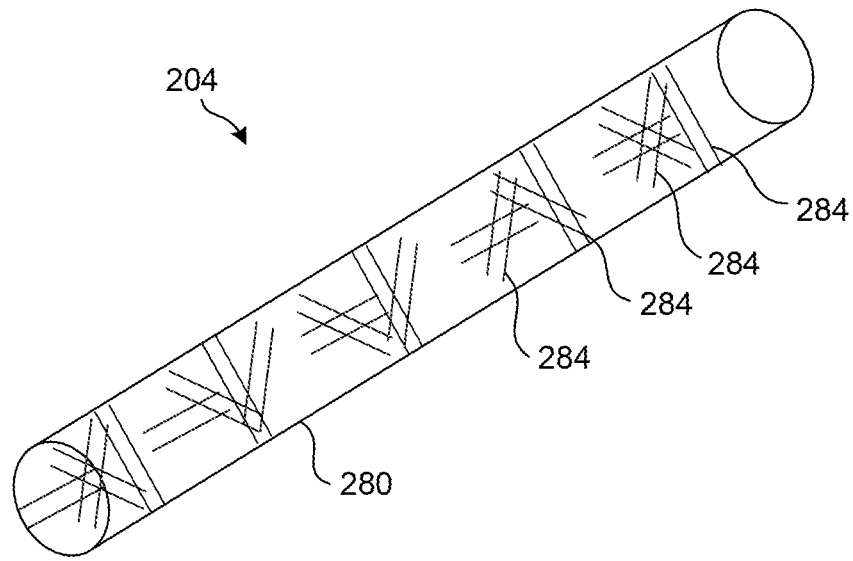
FIG. 5 is a see-through, perspective view of the inflatable member of FIG. 4.
Figure 6A:
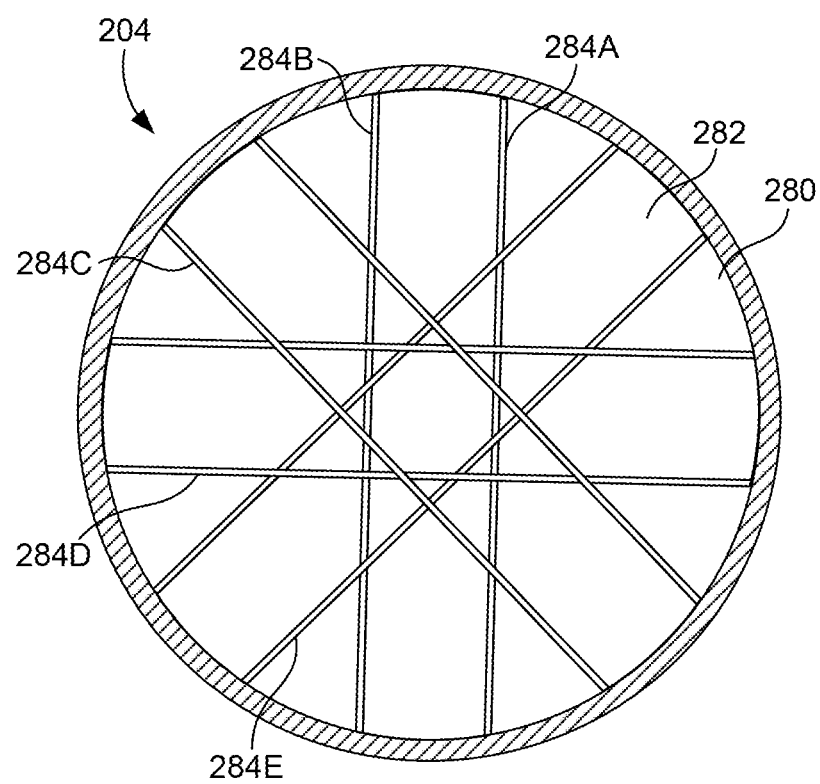
FIG. 6A is a cross-sectional view of the inflatable member of FIG. 4 taken along line A-A of FIG. 4.

FIG. 6A is a cross-sectional view of the inflatable member 204 taken along A-A of FIG. 4. In the illustrated embodiment, some of the structural members 284 are disposed or extend along axes that are parallel or substantially parallel to each other. For example, structural member 284A is parallel or substantially parallel to structural member 284B. Additionally, some of the structural members 284 are disposed or extend along axes that are offset from each other. For example, structural member 284A is offset from structural member 284C and structural member 284E. Additionally, structural member 284A is disposed perpendicular or substantially perpendicular to structural member 284D. In the illustrated embodiment, the structural members 284 do not pass through the center or middle of the inflatable member 204.

Figure 6B:
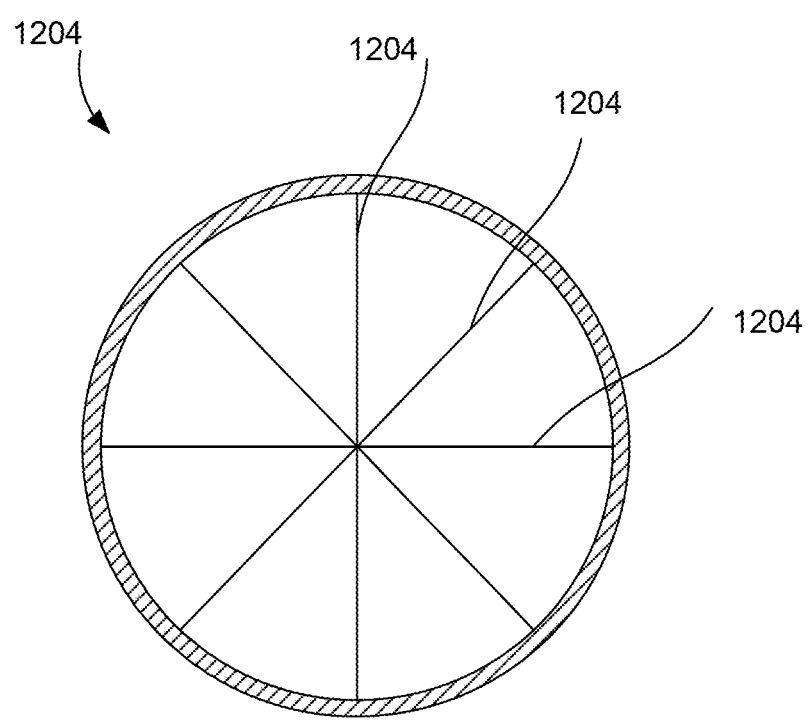
FIG. 6B is a cross-sectional view of an inflatable member of another embodiment.

FIG. 6B is a cross-sectional view of an inflatable member 1204 according to another embodiment. In this embodiment, the series of structural member 1284 all extend through the middle or center of the inflatable member 1204. The structural members 1284 extend radially from the center of the inflatable member 1204. In some embodiments, none of the structural members 1284 extend parallel to another of the structural members 1284. There can be any number of structural members and the structural members can be disposed at any angular orientation.

As best illustrated in FIG. 3, the structural members 284 are also disposed apart from each other along a length or longitudinal axis LA1 of the inflatable member 204.

In some embodiments, the structural member 284 is flexible. In the illustrated embodiment, the structural member 284 is formed of a suture or other filament. Specifically, in the illustrated embodiment, the more than one of the structural members is formed of a single suture or filament. In other embodiments, the structural member is formed of another material. In some embodiments, the structural member is formed of an elastic material. In other embodiments, the structural member is formed of a non-elastic material. In some embodiments, the structural member 284 is a fiber, a filament or a membrane. The structural member 284 may be formed of any type of material.

In the illustrated embodiment, the sidewall 280 is formed of a woven or fabric material. The structural member 284 is coupled to the sidewall at various locations by passing the structural member 284 though the fabric material. In some embodiments, the structural member 284 may be tied or otherwise coupled to the specific location or portion of the fabric material. In other embodiments, the sidewall is formed of another type of material.

In some embodiments, the inflatable member 204 is fluidically sealed. Accordingly, a fluid may be placed within the lumen 282 to inflate the inflatable member 204. In some embodiments, the fabric material of the sidewall 280 is coated with a polymer to fluidically seal the lumen 282. For example, the fabric material may be dipped in a polymer to coat the device. In some embodiments, the inner and outer surface of the fabric material may be coated or have a coating. In some embodiments, the inflatable member 204 may be disposed within an outer tubular member or casing.

The pump assembly 201 may switch between an inflation mode in which the fluid in the reservoir 202 is transferred to the inflatable member 204 (or inflatable members) through the pump assembly 201 in a first direction (e.g., inflation direction) and a deflation mode in which the fluid in the inflatable member 204 (or inflatable members) is transferred back to the reservoir 202 through the pump assembly 201 in a second direction (e.g., deflation direction).

Figure 9:
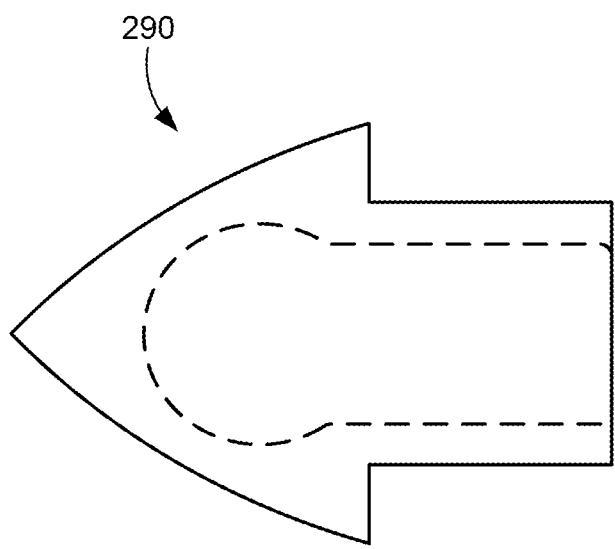
FIG. 9 is an end view of the inflatable member of FIG. 8 during the manufacturing of the inflatable member.

FIG. 9 is an end cap 290 that may be coupled to the end portions of the sidewall 280. In some embodiments, an end cap 290 is coupled to each of the end portions of the sidewall. In some embodiments, the end caps 290 help facilitate the fluidic sealing of the lumen 282. The end caps 290 may be coupled to the end portions of the sidewall via an adhesive or any other know coupling method. In some embodiments, the end cap may be shaped as the ends, tips or caps 224 or 232.

The pump assembly 201 includes a pump bulb member or pump 231, a valve body 233, and a selection member 239. The selection member may be used to select or change the mode in which the pump assembly 201 is in. For example, the selection member 239 may be moved from a first position to a second position to place the device in its deflation mode. The selection member 239 may then be moved back to its first position to place the device in its inflation mode. In some embodiments, the selection member 239 is movable with respect to the valve body 233. For example, the selection member 239 may be slidably coupled or slideable with respect to the valve body 233. In some embodiments, the selection member 239 includes stop members, such as shoulders or detents that engage members of the valve body 233 to lock or help retain the selection member 239 in one of its first and second positions. In other embodiments, the selection member 239 may be disposed or coupled to another portion of the device.

The pump 231 may be squeezed or depressed by the user in order to facilitate the transfer of fluid from the reservoir 202 to the inflatable member 204. For example, in the inflation mode, while the user is operating the pump 231, the pump 231 may receive the fluid from the reservoir 202, and then output the fluid to the inflatable member 204. When the user switches to the deflation mode, at least some of the fluid can automatically be transferred back to the reservoir 202 (due to the difference in pressure from the inflatable member 204 to the reservoir 202). Then, the user may squeeze the inflatable member 204 to facilitate the further transfer of fluid through the pump 231 to the reservoir 202.

Then, when the user wants to deflate the inflatable members 204, the user moves selection member 239 to its deflate position. The user may then operate the pump 231 to deflate the inflatable members 204 (i.e., move the fluid from the inflatable members 204 to the reservoir 202). For example, the user may repeatedly depress or squeeze the pump 231 until the deflation is completed. The pump 231 may then return to its original form, which provides a suction force causing fluid to be drawn into the pump 231 from the inflation members 204. The fluid from the inflation members 204 fills the pump 231 (or at least partially fills the pump 231). This pump cycle is repeated until the inflatable members 204 are deflated.

In some examples, the fluid may automatically (upon movement of the selection member 239 to its deflate position) flow out of the inflatable member 204 and into the reservoir 202 without the user depressing or squeezing the pump 231 until the pressure is at least partially equalized between the reservoir 202 and the inflatable member 204.

In some examples, after the inflation member 204 has been deflated, the pump 231 may be squeezed to place the pump in a contracted position or configuration.

Figure 7:
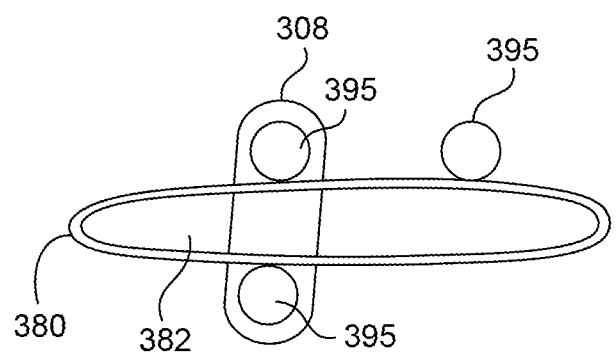
FIG. 7 is a perspective view of a tip member.
Figure 8:
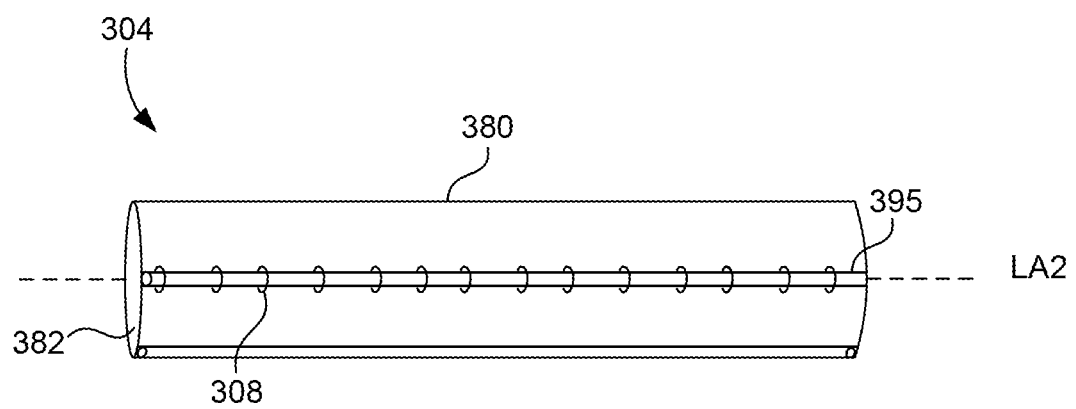
FIG. 8 is a side view of an inflatable member according to an embodiment during the manufacturing of the inflatable member.

FIGS. 7 and 8 illustrate an inflatable member 304 during a manufacturing process according to an embodiment. In some embodiments, the structural member 308 is passed through the sidewall 380 at different locations. Specifically, the structural member 308 may be passed through a first portion of the sidewall 380, through the lumen 382, and through a second portion of the sidewall 380. The structural member 308 may then be passed through yet another portion of the sidewall and through the lumen again. This process can be repeated down the length (along the longitudinal axis LA2) of the inflatable member 304. In the illustrated embodiment, a dowel or rod member 395 may be used in during the manufacturing process to allow for enough material of the structural member to be used. Once the structural member is passed through the sidewall at all of the desired locations along the longitudinal axis, the rod member 395 may be removed or pulled away from the inflatable member. In some embodiments, more than one dowel or rod member 395 may be used in the process. For example, the structural member may pass around more than one dowel or rod member 395 prior to removal of the dowels or rod members 395 from the device.

Figure 10:
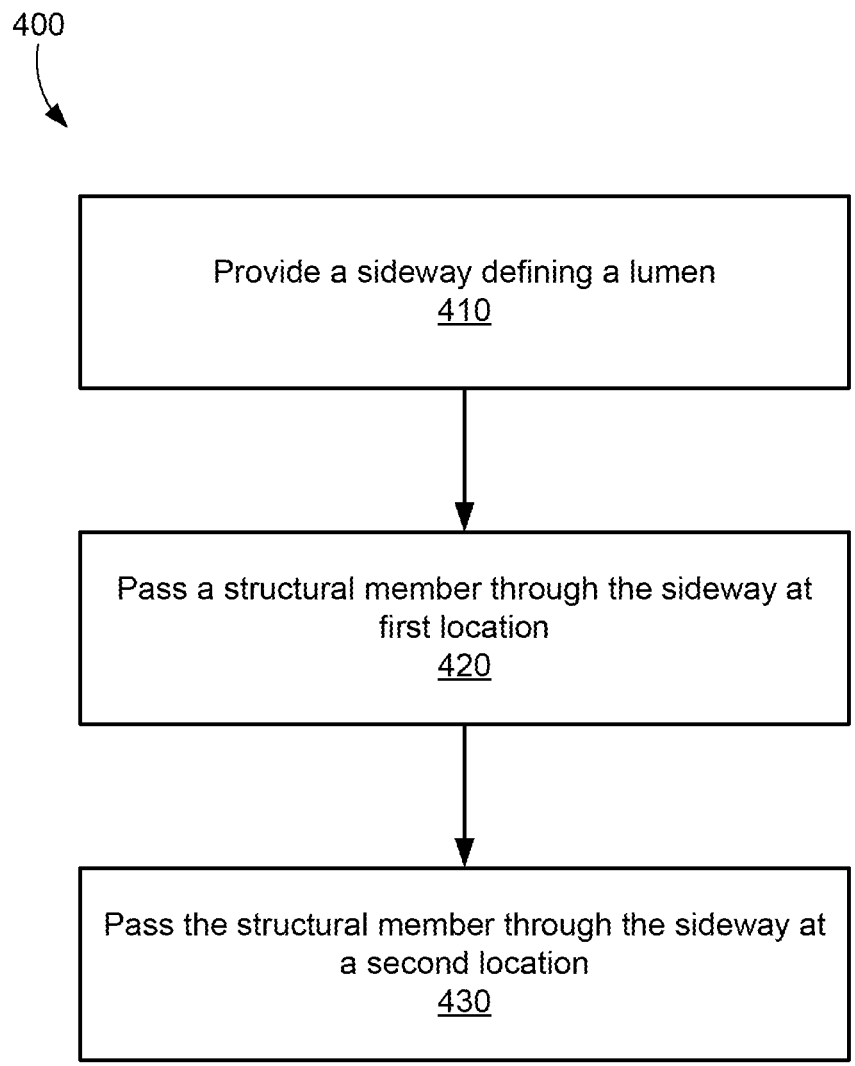
FIG. 10 is a flow chart of a method of making an inflatable member of a penile prosthesis according to an embodiment.

FIG. 10 is a flow chart for a method 400 of making or manufacturing an inflatable member according to an embodiment. At 410, a sidewall defining or having a lumen is provided. At 420, a structural member is passed through a portion of the sidewall at a first location. At 430, the structural member is passed through the sidewall at a second, different location.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. An implant, comprising:
    an inflatable member; and
    a pump assembly configured to facilitate a transfer of a fluid from a reservoir to the inflatable member,
    the inflatable member having a sidewall defining a lumen, the inflatable member including a structural member, the structural member having a first portion that extends through the sidewall at a first location, a second portion that is disposed within the lumen, and a third portion that extends through the sidewall at a second location, the second location being different than the first location.

2. The implant of claim 1, wherein the structural member is flexible.

3. The implant of claim 1, wherein the structural member is a suture, a fiber, a filament or a membrane.

4. The implant of claim 1, wherein the structural member is a first structural member, the inflatable member including a second structural member disposed within the lumen, the second structural member being different than the first structural member.

5. The implant of claim 1, wherein the structural member is a first structural member, the inflatable member including a second structural member disposed within the lumen, the first structural member being disposed substantially parallel to the second structural member.

6. The implant of claim 1, wherein the structural member is a first structural member, the inflatable member including a second structural member disposed within the lumen, the first structural member being disposed substantially perpendicular to the second structural member.

7. The implant of claim 1, wherein the inflatable member extends along a longitudinal axis, the structural member is a first structural member, the inflatable member including a second structural member disposed within the lumen, the first structural member is longitudinally spaced from the second structural member.

8. The implant of claim 1, wherein sidewall is formed of a woven fabric, the inflatable member includes a coating disposed on an outer surface of the sidewall.

9. The implant of claim 1, further comprising:
    a first cap coupled to a first end portion of the inflatable member; and
    a second cap coupled to a second end portion of the inflatable member.

10. The implant of claim 1, wherein the structural member is a first structural member, the inflatable member including a second structural member and a third structural member, the second structural member being disposed within the lumen, the third structural member being disposed within the lumen, the first structural member being different than the second structural member, the first structural member being different than the third structural member, and the second structural member being different than the second structural member.

11. The implant of claim 1, wherein the structural member is a first structural member, the inflatable member including a second structural member and a third structural member, the second structural member being disposed within the lumen, the third structural member being disposed within the lumen, the first structural member being different and offset from the second structural member and the third structural member, the second structural member being different and offset from the third structural member.

12. The implant of claim 1, further comprising:
    a reservoir configured to hold fluid,
    wherein the pump is configured to help facilitate a transfer of the fluid from the inflatable member to the reservoir when the implant is in a deflation mode.

13. The implant of claim 1, wherein the pump assembly includes a valve housing and a pump bulb member.

14. A bodily implant, comprising:
    an inflatable member, the inflatable member having a sidewall defining a lumen and including a structural member, the structural member having a first portion that extends through the sidewall at a first location, a second portion that is disposed within the lumen, and a third portion that extends through the sidewall at a second location, the second location being different than the first location.

15. The bodily implant of claim 14, wherein the sidewall is formed of a woven fabric.

16. The bodily implant of claim 14, wherein the sidewall is formed of a woven fabric, a coating being disposed on an outer surface of the fabric.

17. A method of making a bodily implant, comprising:
    providing a member that includes a sidewall that defines a lumen;
    passing a structural member through the sidewall at a first location of the sidewall; and
    passing the structural member through a portion of the lumen.

18. The method of claim 17, further comprising:
    passing the structural member through the sidewall at a second location of the sidewall, the second location of the sidewall being different than the first location of the sidewall.

19. The method of claim 17, further comprising:
passing the structural member around a portion of a rod member.

* * * * *